(12) United States Patent
Mettauer et al.

(10) Patent No.: US 11,759,611 B2
(45) Date of Patent: Sep. 19, 2023

(54) INTEGRATED CATHETER ASSEMBLY

(71) Applicant: EVOLVE MEDICUS, INC., Gainesville, FL (US)

(72) Inventors: Mark Menefee Mettauer, The Woodlands, TX (US); Steve Lepke, Wakefield, MA (US)

(73) Assignee: EVOLVE MEDICUS, INC., Gainesville, FL (US)

(*) Notice: Subject to any disclaimer, the term of this patent is extended or adjusted under 35 U.S.C. 154(b) by 179 days.

(21) Appl. No.: 17/396,837

(22) Filed: Aug. 9, 2021

(65) Prior Publication Data
US 2023/0042163 A1 Feb. 9, 2023

(51) Int. Cl.
*A61M 25/06* (2006.01)
*A61M 1/36* (2006.01)
(Continued)

(52) U.S. Cl.
CPC ...... *A61M 25/0662* (2013.01); *A61M 1/3655* (2013.01); *A61M 1/3661* (2014.02);
(Continued)

(58) Field of Classification Search
CPC ............ A61M 25/0662; A61M 1/3655; A61M 1/3661; A61M 25/0606; A61M 25/0637; A61M 25/0643; A61M 25/0693; A61M 39/10; A61M 2025/0008; A61M 2025/0687; A61M 25/065; A61M 2025/0681
See application file for complete search history.

(56) References Cited

U.S. PATENT DOCUMENTS 3,094,122 A 6/1963 Gauthier
3,313,299 A 4/1967 Spademan
(Continued)

FOREIGN PATENT DOCUMENTS

EP 0000041 B1 12/1978
EP 0191599 B1 8/1991
GB 2088215 A 6/1982

*Primary Examiner* — Susan S Su
*Assistant Examiner* — Ted Yang
(74) *Attorney, Agent, or Firm* — Marc L Delflache; JONES DELFLACHE LLP

(57) ABSTRACT

An integrated catheter assembly includes a housing member, an outer lumen member extending from the housing member, and a needle member slidably or movably coupled to the housing member, wherein the needle member can be extended beyond a first port of the outer lumen member in a first position and concealed in the outer lumen member in a second position. The outer lumen member has a side port between its first and second ports such that when the needle is extended in the first position and inserted into an arteriovenous fistula, blood from the arteriovenous fistula flashes into the needle member, is diverted through a relief port of the needle member out the side port of the outer lumen member for delivery to a dialysis machine. The assembly further includes an inner lumen member that is disposable through the housing member to extend out from the same the outer lumen member to provide dialyzed blood from the machine. The assembly therefore receives and delivers blood through a single injection site.

15 Claims, 21 Drawing Sheets

(51) Int. Cl.
*A61M 39/10* (2006.01)
*A61M 25/00* (2006.01)

(52) U.S. Cl.
CPC .... *A61M 25/0606* (2013.01); *A61M 25/0637* (2013.01); *A61M 25/0643* (2013.01); *A61M 25/0693* (2013.01); *A61M 39/10* (2013.01); *A61M 2025/0008* (2013.01); *A61M 2025/0687* (2013.01)

(56) References Cited

U.S. PATENT DOCUMENTS

| | | | |
|---|---|---|---|
| 3,399,674 A * | 9/1968 | Pannier | A61M 25/065 |
| | | | D24/112 |
| 3,537,451 A | 11/1970 | Beck | |
| 3,584,624 A | 6/1971 | Ciutiis | |
| 3,734,095 A | 5/1973 | Santomieri | |
| 3,766,916 A | 10/1973 | Moorehead | |
| 4,016,879 A | 4/1977 | Mellor | |
| 4,037,599 A * | 7/1977 | Raulerson | A61M 5/1582 |
| | | | 604/533 |
| 4,099,528 A | 7/1978 | Sorenson | |
| 4,177,809 A | 12/1979 | Moorehead | |
| 4,202,332 A | 5/1980 | Tersteegen | |
| 4,270,535 A | 6/1981 | Bogue | |
| 4,543,087 A | 9/1985 | Sommercom | |
| 4,583,968 A | 4/1986 | Mahurkar | |
| 4,770,652 A | 9/1988 | Mahurkar | |
| 4,776,841 A | 10/1988 | Catalano | |
| 4,808,155 A | 2/1989 | Mahurkar | |
| 4,867,743 A | 9/1989 | Vaillancourt | |
| 4,935,008 A | 6/1990 | Lewis | |
| 5,108,375 A | 4/1992 | Harrison | |
| 5,188,593 A | 2/1993 | Martin | |
| 5,312,361 A * | 5/1994 | Zadini | A61M 5/158 |
| | | | 604/233 |
| 5,352,205 A | 10/1994 | Dales | |
| 5,364,344 A | 11/1994 | Beattie | |
| 5,405,341 A | 4/1995 | Martin | |
| 5,407,431 A * | 4/1995 | Botich | A61M 25/0631 |
| | | | 604/110 |
| 5,486,159 A | 1/1996 | Mahurkar | |
| 5,776,096 A | 7/1998 | Fields | |
| 5,876,366 A | 3/1999 | Dykstra | |
| 5,919,163 A | 7/1999 | Glickman | |
| 5,976,103 A * | 11/1999 | Martin | A61M 1/3661 |
| | | | 604/35 |
| 6,238,369 B1 | 5/2001 | Burbank | |
| 6,508,790 B1 | 1/2003 | Lawrence | |
| 6,692,473 B2 | 2/2004 | St Cyr et al. | |
| 6,786,875 B2 * | 9/2004 | Barker | A61B 5/1535 |
| | | | 604/164.12 |
| 6,962,575 B2 * | 11/2005 | Tai | A61M 1/3661 |
| | | | 604/164.01 |
| 6,966,886 B2 | 11/2005 | Appling | |
| 7,008,395 B1 | 3/2006 | Loggie | |
| 7,282,041 B2 | 10/2007 | Igarashi | |
| 7,381,204 B2 | 6/2008 | Wilson | |
| 7,413,560 B2 * | 8/2008 | Chong | A61M 25/0637 |
| | | | 604/164.08 |
| 7,575,563 B2 | 8/2009 | Appling | |
| 7,846,127 B2 | 12/2010 | Igarashi | |
| 8,021,321 B2 | 9/2011 | Zawacki | |
| 8,241,245 B2 | 8/2012 | Markel | |
| 8,343,104 B2 | 1/2013 | Martin | |
| 8,496,607 B2 | 7/2013 | Feng | |
| 8,892,182 B2 | 11/2014 | Matonick | |
| 9,005,154 B2 | 4/2015 | Matson | |
| 9,168,352 B2 | 10/2015 | Kelly | |
| 9,233,223 B2 | 1/2016 | Shorey | |
| 9,233,230 B2 | 1/2016 | Puhasm | |
| 9,415,187 B2 | 8/2016 | Agnew | |
| 9,782,534 B2 | 10/2017 | Kelly | |
| 9,867,926 B2 | 1/2018 | Defonzo | |
| 9,925,353 B2 | 3/2018 | Shorey | |
| 10,265,506 B2 * | 4/2019 | Borowicz | A61M 5/3243 |
| 10,279,101 B2 | 5/2019 | Kelly | |
| 10,321,933 B1 * | 6/2019 | Ramee | A61M 39/06 |
| 10,363,390 B2 | 7/2019 | Tal | |
| 11,229,730 B2 * | 1/2022 | Teo | A61M 1/3661 |
| 11,294,755 B2 | 4/2022 | Shidham | |
| 11,344,659 B2 | 5/2022 | Kelly | |
| 2004/0193119 A1 | 9/2004 | Canaud | |
| 2004/0210180 A1 | 10/2004 | Altman | |
| 2005/0004504 A1 | 1/2005 | Frye | |
| 2005/0096609 A1 * | 5/2005 | Maginot | A61M 1/3659 |
| | | | 604/271 |
| 2005/0107820 A1 * | 5/2005 | Forsberg | A61M 29/00 |
| | | | 606/194 |
| 2006/0155244 A1 * | 7/2006 | Popov | A61M 25/0625 |
| | | | 604/110 |
| 2006/0276773 A1 | 12/2006 | Wilson | |
| 2007/0073237 A1 | 3/2007 | Rodd | |
| 2007/0073239 A1 | 3/2007 | Skansen | |
| 2008/0009784 A1 | 1/2008 | Leedle | |
| 2008/0108969 A1 | 5/2008 | Andrew | |
| 2008/0312577 A1 | 12/2008 | Drasler | |
| 2009/0054845 A1 | 2/2009 | Ame | |
| 2009/0216174 A1 | 8/2009 | Nardeo | |
| 2010/0076406 A1 | 3/2010 | Raulerson | |
| 2010/0204635 A1 | 8/2010 | Haarala | |
| 2010/0331644 A1 * | 12/2010 | Neale | A61N 1/05 |
| | | | 600/345 |
| 2011/0125097 A1 | 5/2011 | Shaw | |
| 2013/0303966 A1 | 4/2013 | Haarala | |
| 2013/0150767 A1 * | 6/2013 | Tsyrulnykov | A61M 1/3656 |
| | | | 604/5.04 |
| 2013/0158483 A1 | 6/2013 | Senitko | |
| 2013/0199722 A1 * | 8/2013 | Burbank | A61M 5/365 |
| | | | 29/455.1 |
| 2013/0304033 A1 * | 11/2013 | DeFonzo | A61M 1/3661 |
| | | | 604/524 |
| 2014/0094774 A1 * | 4/2014 | Blanchard | A61M 25/0097 |
| | | | 604/164.08 |
| 2014/0221932 A1 * | 8/2014 | Puhasmagi | A61M 25/0606 |
| | | | 604/167.05 |
| 2014/0276588 A1 * | 9/2014 | Li | A61M 25/0097 |
| | | | 604/117 |
| 2015/0173782 A1 * | 6/2015 | Garrison | A61M 25/0068 |
| | | | 606/127 |
| 2015/0231364 A1 * | 8/2015 | Blanchard | A61M 25/0618 |
| | | | 604/164.08 |
| 2016/0008538 A1 * | 1/2016 | Isaacson | A61M 5/158 |
| | | | 604/263 |
| 2016/0256667 A1 * | 9/2016 | Ribelin | A61M 25/09041 |
| 2016/0279318 A1 | 9/2016 | Tsyrulnykov | |
| 2016/0296728 A1 * | 10/2016 | Smith | A61M 1/3659 |
| 2017/0080181 A1 | 3/2017 | Shiono | |
| 2017/0136207 A1 | 5/2017 | Shiono | |
| 2017/0239443 A1 * | 8/2017 | Abitabilo | A61M 39/10 |
| 2017/0354416 A1 * | 12/2017 | Dickinson | A61B 34/20 |
| 2018/0117266 A1 * | 5/2018 | Grant | A61B 18/24 |
| 2018/0133438 A1 * | 5/2018 | Hulvershorn | A61M 25/0113 |
| 2018/0214682 A1 * | 8/2018 | Woehr | A61M 39/0613 |
| 2018/0256862 A1 * | 9/2018 | Bagwell | A61M 25/0113 |
| 2018/0264235 A1 * | 9/2018 | Bierman | A61M 25/0606 |
| 2018/0289939 A1 | 10/2018 | Mason | |
| 2018/0296804 A1 * | 10/2018 | Bierman | A61M 39/0247 |
| 2019/0046764 A1 * | 2/2019 | Ueda | A61M 25/0097 |
| 2019/0070393 A1 * | 3/2019 | Khalaj | A61M 25/0606 |
| 2019/0247090 A1 * | 8/2019 | Armstrong | A61M 25/09041 |
| 2019/0351192 A1 * | 11/2019 | Bierman | A61B 17/3415 |
| 2019/0381234 A1 * | 12/2019 | Shidham | A61M 1/14 |
| 2019/0381235 A1 * | 12/2019 | Shidham | A61M 1/3655 |
| 2020/0061336 A1 | 2/2020 | Bard | |
| 2020/0147349 A1 * | 5/2020 | Holt | A61M 25/09041 |
| 2020/0187918 A1 | 6/2020 | Wiygul | |
| 2021/0023336 A1 * | 1/2021 | Lee | A61M 25/0028 |
| 2021/0077774 A1 | 3/2021 | Kelly | |
| 2021/0178142 A1 | 6/2021 | Sauer | |
| 2021/0187252 A1 * | 6/2021 | Johnson | A61M 25/0606 |
| 2021/0290913 A1 * | 9/2021 | Horst | A61M 25/09 |

(56) References Cited

U.S. PATENT DOCUMENTS

| | | | |
|---|---|---|---|
| 2022/0062596 A1* | 3/2022 | Ribelin | A61M 25/09041 |
| 2022/0134059 A1* | 5/2022 | Lauer | A61M 25/02 604/264 |
| 2022/0226613 A1* | 7/2022 | Shidham | A61M 25/0097 |
| 2022/0241561 A1* | 8/2022 | Pierce | A61M 25/0606 |
| 2023/0012462 A1* | 1/2023 | Ash | A61M 25/0693 |

* cited by examiner

INTEGRATED CATHETER ASSEMBLY

FIELD OF THE INVENTION

The present general inventive concept relates to medical devices for dialysis and more particularly to an integrated catheter for dialysis.

BACKGROUND OF THE INVENTION

Injuries, diseases, or disorders can cause kidney or renal system failure, resulting in a variety of physiological problems. Levels of various fluids and minerals can exceed healthy ranges. Toxic byproducts of bodily processes can then accumulate in blood and tissues, leading to myriad long term negative health consequences.

The present state of the art for addressing kidney or renal system failure is to perform dialysis procedures that are designed to supplement or replace the body's own filtering functions. These procedures, to varying degrees, are effective at removing waste and toxins from the body when a patient's own renal system is unable to do so. Certain patients need more frequent or more extensive dialysis sessions than do others. Regardless, each session can be a mental and physical challenge, and discomfort associated with the procedure is to a significant degree related to the attachment of the patient to the dialysis machine.

For a hemodialysis procedure, a patient is attached to a hemodialysis machine using catheters, one of which removes blood from the patient and the other of which returns blood to the patient. The machine removes waste and toxins from the received blood and returns the filtered blood back to the patient. For each session, the patient must have the catheters inserted into a vein, artery, or surgically created arteriovenous fistula (or shunt), which is an unpleasant procedure, especially when undergone three times per week, which is a frequency of dialysis required for the majority of afflicted patients.

At present, the securing of catheters to the patient involves the following steps. The skin of a first insertion target area of the patient is cleaned, and a tourniquet is applied between the first insertion target area and the shoulder of the patient. A first needle is inserted into the arteriovenous fistula at the first insertion target area, and a flash of blood is observed to indicate that access to the shunt or arteriovenous fistula was successful. Then, the skin of a second insertion target area of the patient is cleaned, the first needle is secured to the arm of the patient using multiple rounds of tape, and the tube attached to the first needle is clamped to prevent blood flow out from the patient.

A second needle is inserted into the shunt or arteriovenous fistula at the second insertion target area, and a flash of blood is observed to indicate that access to the shunt or arteriovenous fistula was successful. The second needle is secured to the arm of the patient using multiple rounds of tape, and the tube attached to the second needle is clamped to prevent blood flow out from the patient.

Next, the tubes are primed, clamped, and attached to the dialysis machine. Loose portions of the tubes are taped to the patient's shoulder. Finally, the tube clamps and the tourniquet are removed. The dialysis machine then filters blood from the patient for the recommended time. Once the session is complete, the tape and multiple needles must be removed from the patient and hemostasis acquired.

As can easily be understood from even the above cursory description of the current process, the attachment of the patient to the dialysis machine is uncomfortable at best and painful at worst.

For the above reasons, there is a need for improved catheter devices and configurations, and particularly catheter devices and configurations that decrease discomfort and pain experienced by dialysis patients. The present invention addresses this need and provides additional benefits.

SUMMARY OF THE INVENTION

The present invention provides an integrated catheter assembly and methods of use.

As should be appreciated, the integrated catheter device of the present general inventive concept provides one or more of the following benefits.

Preferred embodiments provide an integrated, all-in-one device, and accordingly reduces confusion, misconfiguration, and the training required to effectively administer the procedure. The tubing management features of the device also contribute to these benefits.

Preferred embodiments increase comfort, at least by use of a 14G needle that is retracted. It can be understood that a 14G needle that is retracted is more comfortable than a 15G needle that remains, as is the case with current catheters. This also increase the flow rate, which reduces the times needed for the dialysis process.

Preferred embodiments provide a single point of entry, reducing needle insertions from 2 to 1. This further reduces the time needed for the procedure, and reduces the potential infection. The current procedure averages 4 hours and 17 minutes. With the present invention, the procedure can be shortened at least to 2 hours and 3 minutes. Based on 12 procedures per month, this reduces needle entries from 24 times to 12 times, and reduces procedure time by: 1 hour, 47 minutes per session, which is 5 hours and 21 minutes per week, which is 21 hours and 24 minutes per month, which is 11 days, 14 hours and 12 minutes per year. This also potentially lowers healthcare costs.

The above benefits and others can be realized by an integrated catheter assembly of the invention. Preferred embodiments of the present invention include a housing member having a first end and an opposing second end; an outer lumen member to extend from the first end of the housing member; and a needle member slidably (or movably) coupled to the housing member, wherein the needle member extends beyond the outer lumen member in a first position and is concealed in a second position.

In preferred embodiments, the catheter assembly further includes a locking feature to releasably lock the needle member at the first and second positions.

Further in preferred embodiments, the outer lumen member includes a plurality of ports in fluidic communication with each other, the plurality of ports including a first port disposed at a first end of the outer lumen member, a second port disposed at an opposing second end, and a third port disposed between the first port and the second port.

Preferably, the needle member includes a sharp tip at a first end and a blunt tip at an opposing second end. Further preferably, the needle member includes a relief port disposed between the first end and the second end. Still further preferably, fluid received by the needle member is diverted by the relief port to the third port when the needle member is disposed at the first position.

Preferably, the catheter assembly further includes a coupling body member attached to the second port of the outer lumen member and configured to receive an inner lumen. Further preferably, the catheter assembly further includes an inner lumen depth gauge coupled to the coupling body member. Still further preferably, the depth gauge includes depth markings and the inner lumen includes an inner lumen depth marker cooperating with the depth markings to indicate a distance from which a first end of the inner lumen member extends past the first port of the outer lumen member.

Further preferably, when the inner lumen is disposed coaxial with the outer lumen and the needle is in the second position, blood flow is permitted between an outer wall of the inner lumen and an inner wall of the outer lumen. Still further preferably, the inner lumen has an outer diameter smaller than an inner diameter of the needle member and the needle member has an outer diameter smaller than an inner diameter of the outer lumen.

Further preferably, the catheter assembly further includes an outflow tube coupled in fluidic communication with the third port and an inflow tube coupled in fluidic communication with the inner lumen member. Still further preferably, the housing member includes at least one channel by which at least one of the tubes can be held adjacent the housing member.

Further preferably, outer surfaces of the housing member are non-parallel such that when the housing member is adjacent a target area of a patient, a longitudinal axis of the outer lumen member and a longitudinal axis of the inner lumen member are angled toward the target area. Still further preferably, the housing member includes at least one adhesive flap contoured to approximate a curvature of an arm.

A method of use of the integrated catheter assembly of preferred embodiments of the present invention includes a method of attaching a patient to a dialysis machine, including the steps of inserting into a target arteriovenous fistula of a patient a needle member coupled to a housing member of an integrated catheter assembly, the needle member extending from a first port of an outer lumen member extending from the housing member, the outer lumen member having a second port opposite the first port and configured to accept an inner lumen; observing a flash of blood at a third port of the outer lumen member, the third port positioned between the first and second ports, the blood having passed into the needle member, out a relief port of the needle member and into the third port of the outer lumen member; retracting the needle member into the outer lumen until blood flows into the first port and directly out the third port; inserting the inner lumen into the second port of the outer lumen until the inner lumen extends from the first port of the outer lumen and into the arteriovenous fistula; and connecting to the dialysis machine an outflow tube in fluidic communication with the third port of the outer lumen member, and an inflow tube in fluidic communication with the inner lumen member.

In preferred embodiments, the method further includes passing the inner lumen adjacent an inner lumen depth gauge. Preferably, the method further includes aligning a depth marker to a desired depth marking of the depth gauge to establish a desired distance from which a first end of the inner lumen member extends past the first port of the outer lumen member.

In preferred embodiments, the method further includes disposing the inner lumen coaxial with the outer lumen. Preferably, the inner lumen has an outer diameter smaller than an inner diameter of the needle member and the needle member has an outer diameter smaller than an inner diameter of the outer lumen.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

BRIEF DESCRIPTION OF THE DRAWINGS

In FIG. 1A the lumen member is inserted in the housing member. In FIG. 1B the lumen member is inserted in the housing member. Unless otherwise indicated, references herein to FIG. 1 shall mean FIGS. 1A and 1B.

FIG. 7B illustrates in dashed lines internal features not visible in FIG. 7A. Unless otherwise indicated, references herein to FIG. 7 shall mean FIGS. 7A and 7B.

FIGS. 8A-1, 8A-2 and 8B are side views that illustrate non-parallel outer surfaces of a housing member of an integrated catheter device according to an example of the present general inventive concept. Dashed lines show internal features. Unless otherwise indicated, references herein to FIG. 8 shall mean FIGS. 8A-1, 8A-2 and 8B.

FIG. 10A illustrates in dashed lines internal features shown transparently in FIG. 10B. Unless otherwise indicated, references herein to FIG. 10 shall mean FIGS. 10A and 10B.

DETAILED DESCRIPTION OF PREFERRED EMBODIMENTS

Figure 1A:
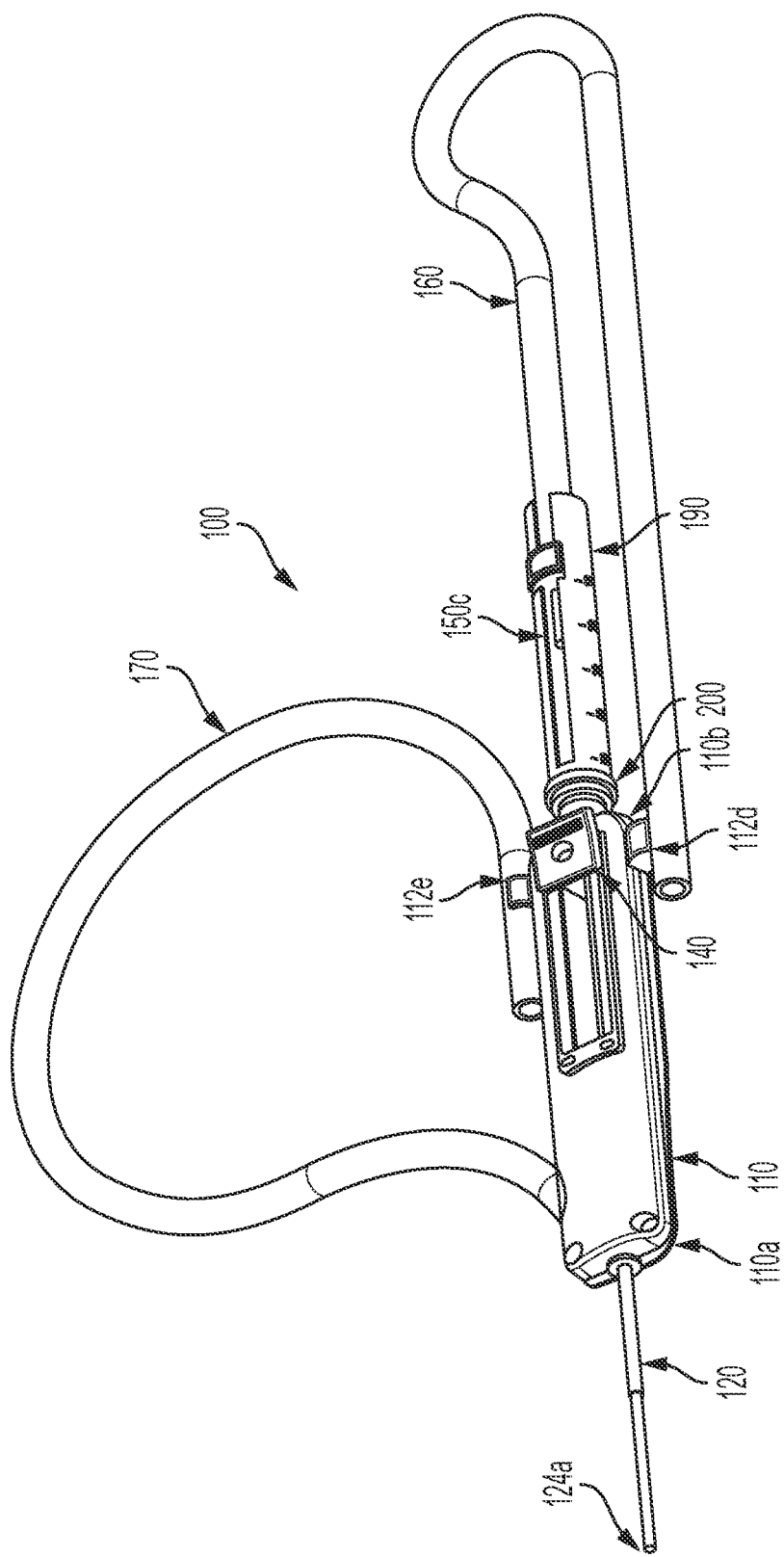
FIGS. 1A and 1B are front perspective and side views, respectively, of an integrated catheter device according to an example of the present general inventive concept, showing a housing member with a needle member (not visible) retracted and an inner lumen member that cooperates with the housing member.
Figure 1B:
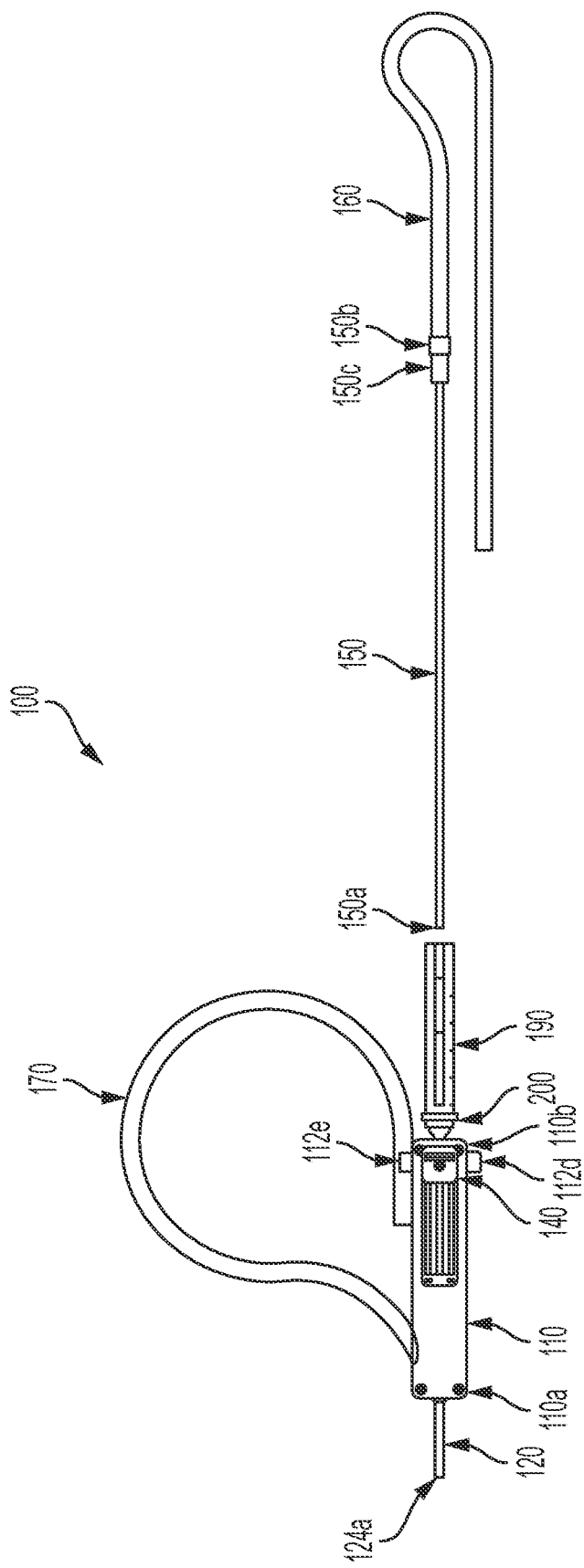
Figure 2:
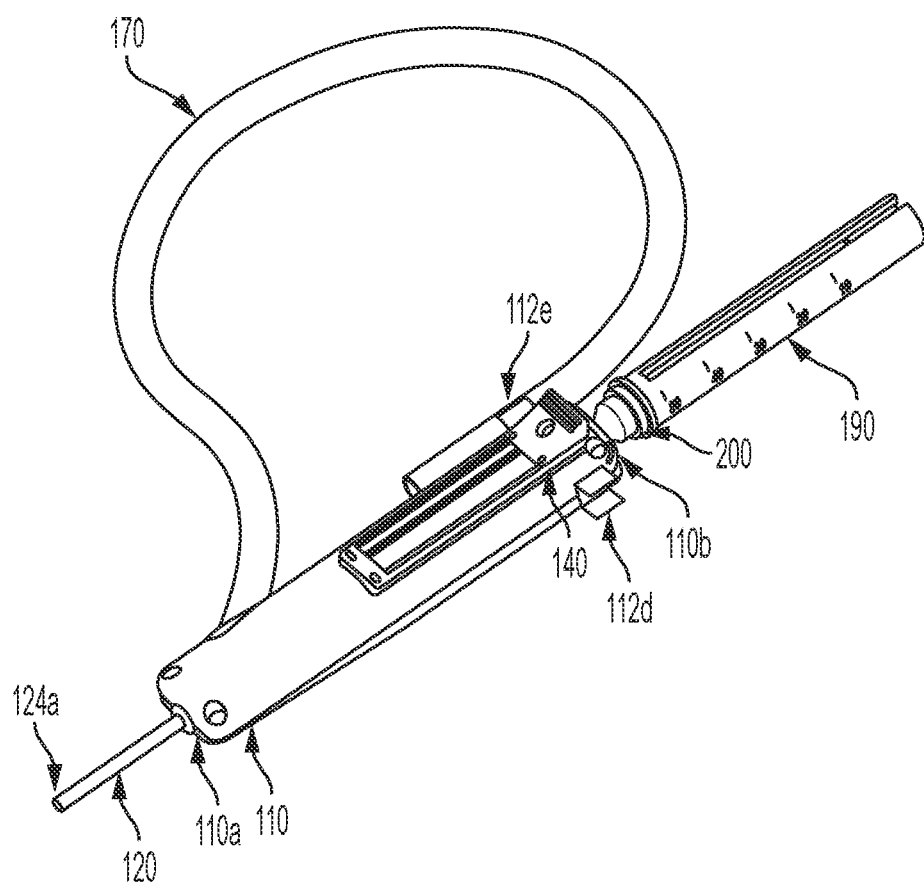
FIG. 2 is a front perspective view of the housing member of FIG. 1, with the needle member (not visible) retracted.
Figure 3:
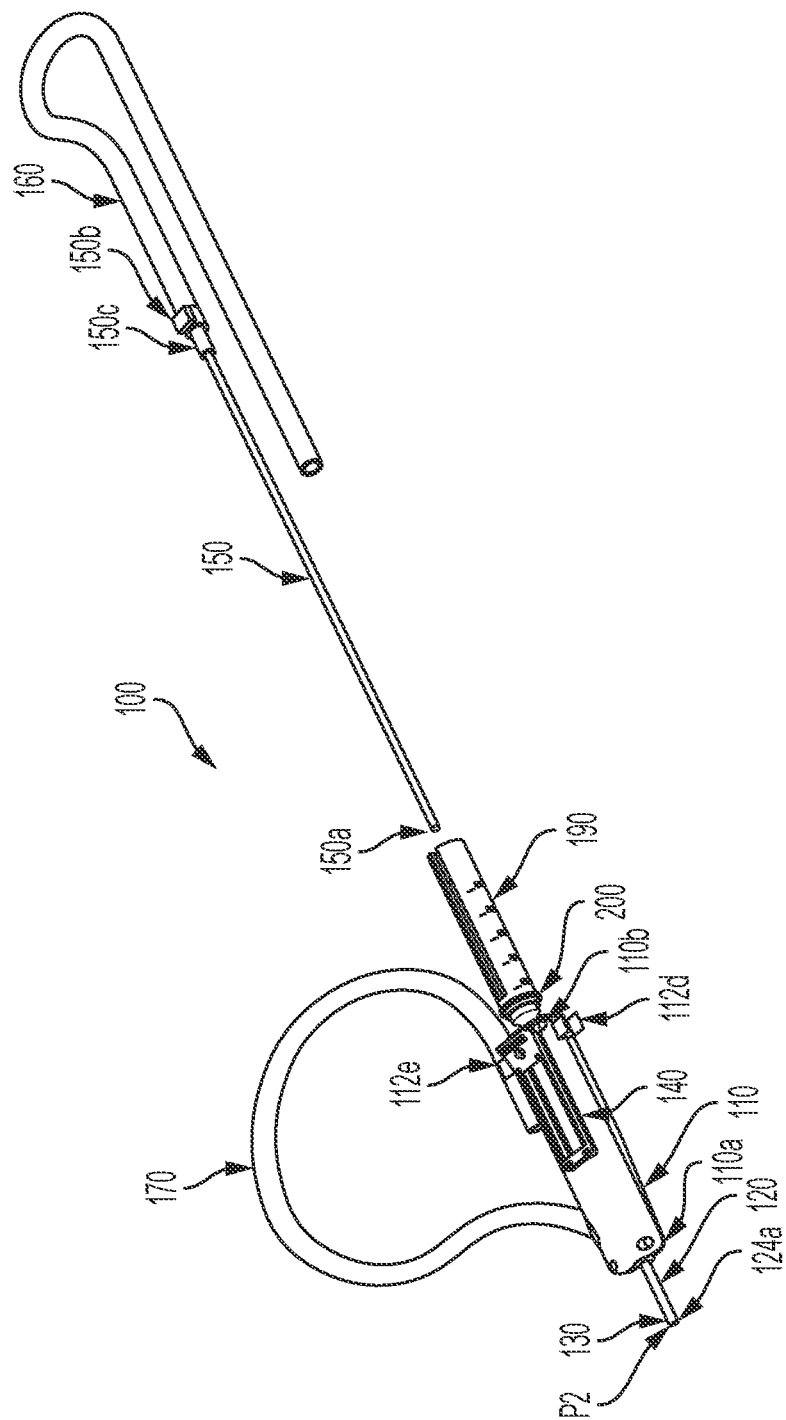
FIG. 3 is a front perspective view of the integrated catheter device of FIG. 1, showing the housing member with the needle member extended and the inner lumen member that cooperates with the housing member.
Figure 4:
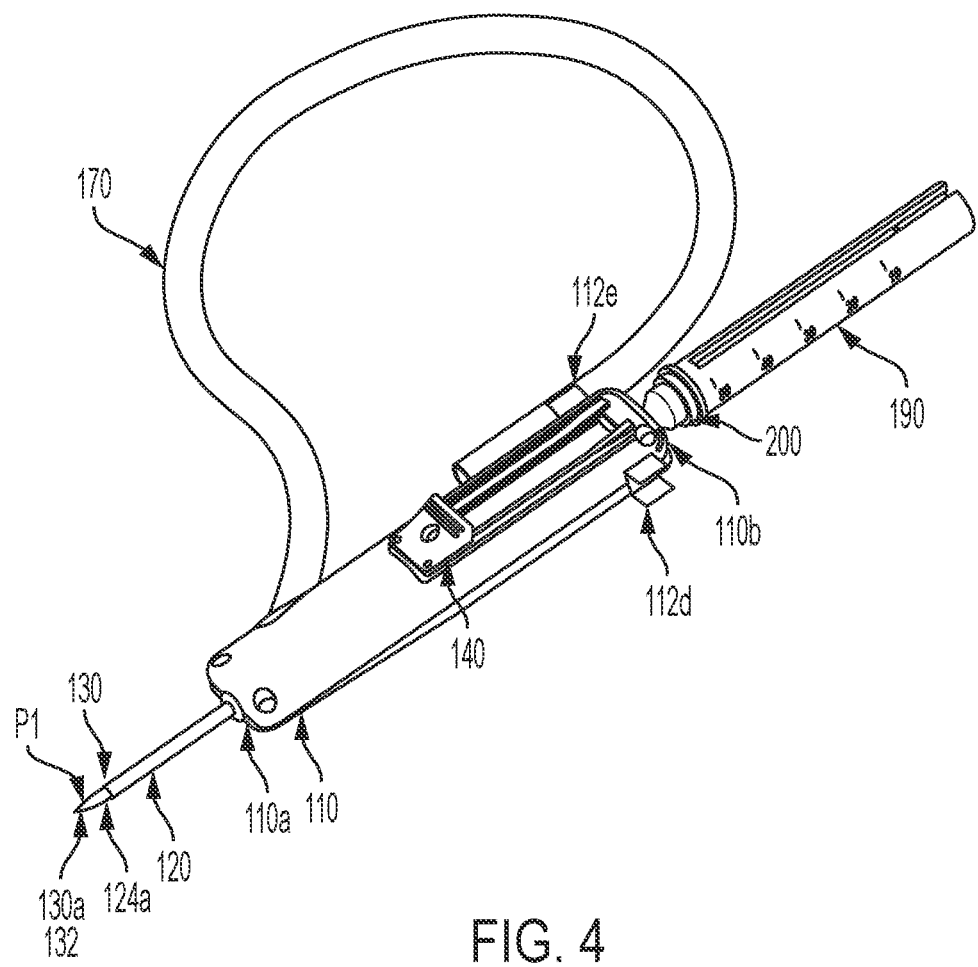
FIG. 4 is a front perspective view of the housing member of FIG. 1, with the needle member extended.

Reference will now be made in detail to the exemplary embodiments of the present general inventive concept, examples of which are illustrated in the accompanying drawings, wherein like reference numerals refer to the like elements throughout. The exemplary embodiments are described below in order to explain the present general inventive concept by referring to the figures. It is understood that the drawings provided herein are representations of exemplary embodiments of the present general inventive concept and are neither limiting nor drawn to scale.

Referring to FIGS. 1-6, in an example embodiment, an integrated catheter device 100 includes a housing member 110 having a first end 110a and an opposing second end 110b, an outer lumen member 120 designed to extend from the first end 110a of the housing member 110, and a needle member 130 (visible in FIGS. 3-6) slidably (or movably) coupled to the housing member 110. The integrated catheter device 100 further includes an inner lumen member 150 disposable through the housing member 110 and outer lumen member 120 (e.g., the inner lumen member 150 has an outer diameter smaller than an inner diameter of the outer lumen member 120). The housing member 110 includes a coupling body member 200 at the second end 110b of the housing member 110 by which the inner lumen member 150 can be coupled to the housing member 110 to secure the inner lumen member 150 relative to the outer lumen member 120. Preferably, the coupling body member 200 is a luer lock.

Figure 5:
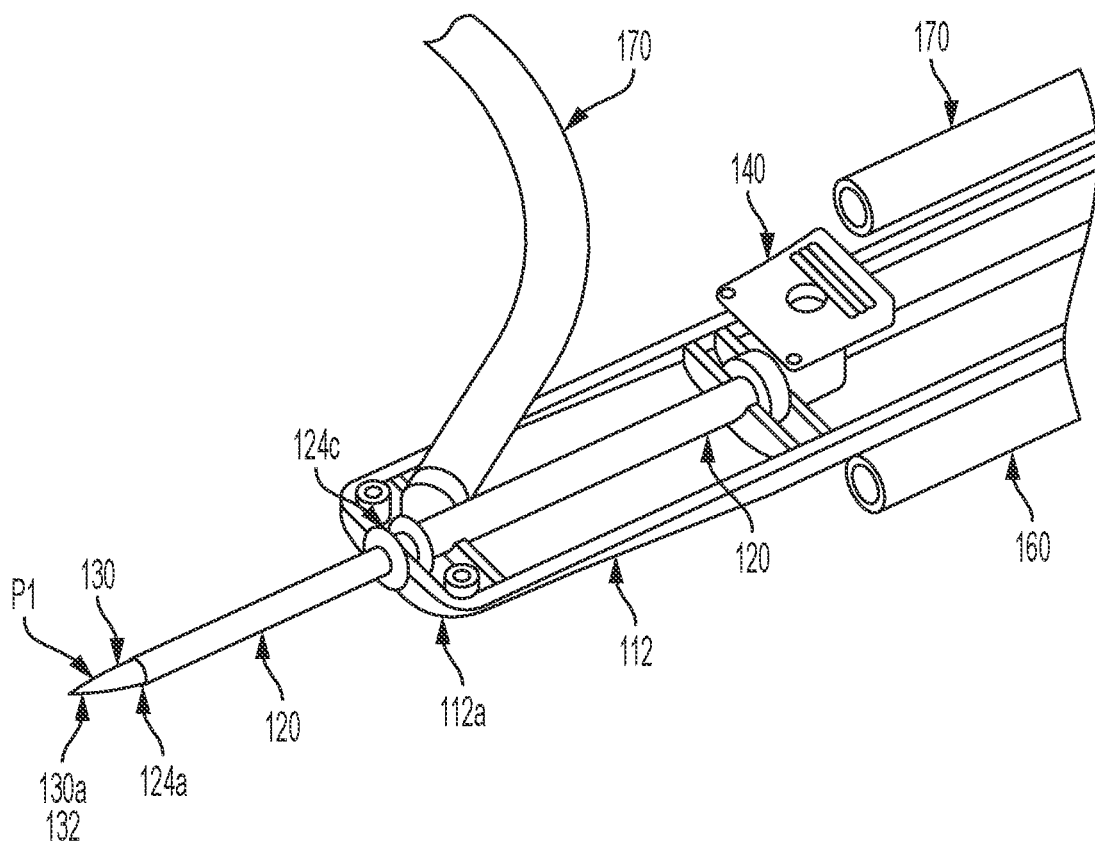
FIG. 5 is a front perspective view of the forward portion of the housing member of FIG. 1, with a housing cover removed and the needle member retracted.
Figure 6:
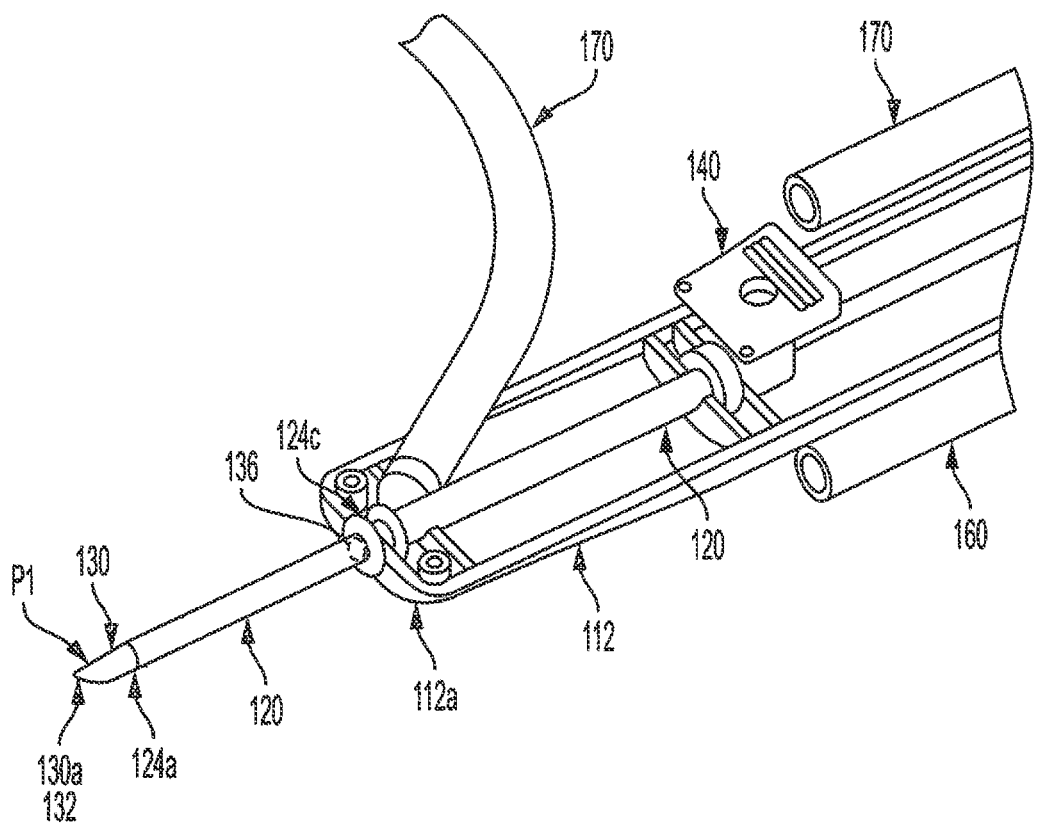
FIG. 6 is a front perspective view of the forward portion of the housing member of FIG. 1, with a housing cover removed and the needle member extended.
Figure 7A:
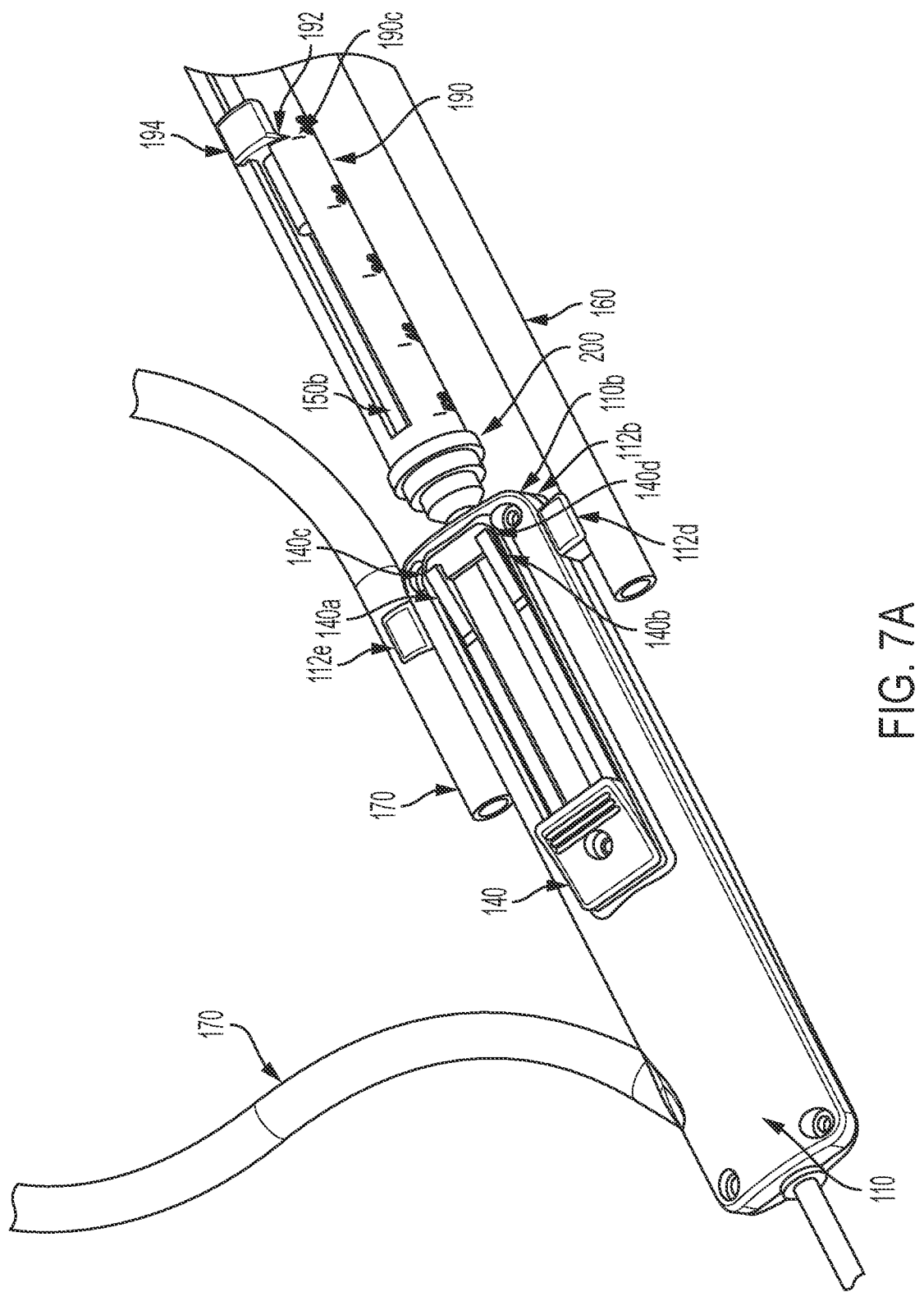
FIGS. 7A and 7B are top perspective views that illustrate locking slide button features of an integrated catheter device according to an example of the present general inventive concept.
Figure 7B:
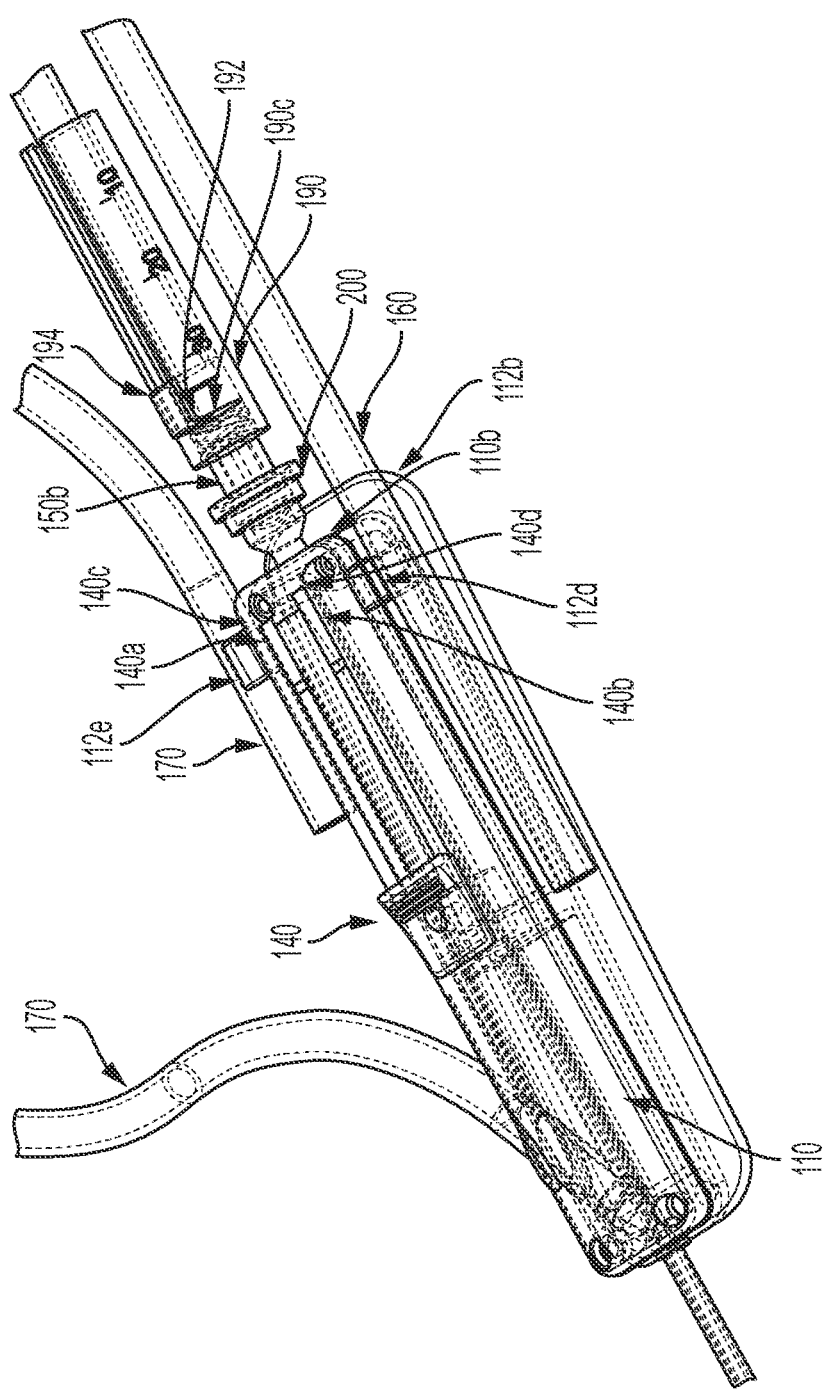
Figures 1, 8A:
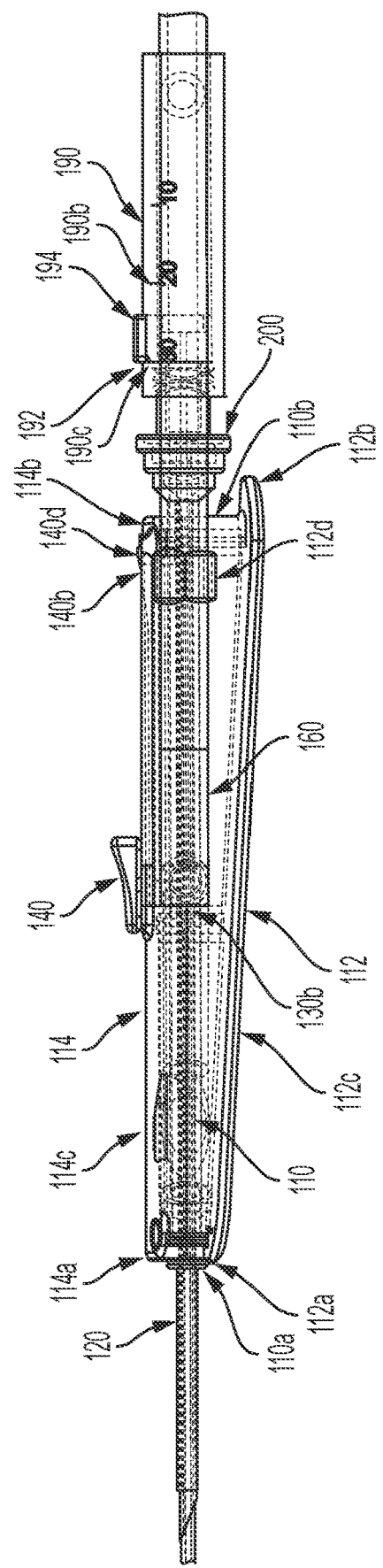
Figures 2, 8A:
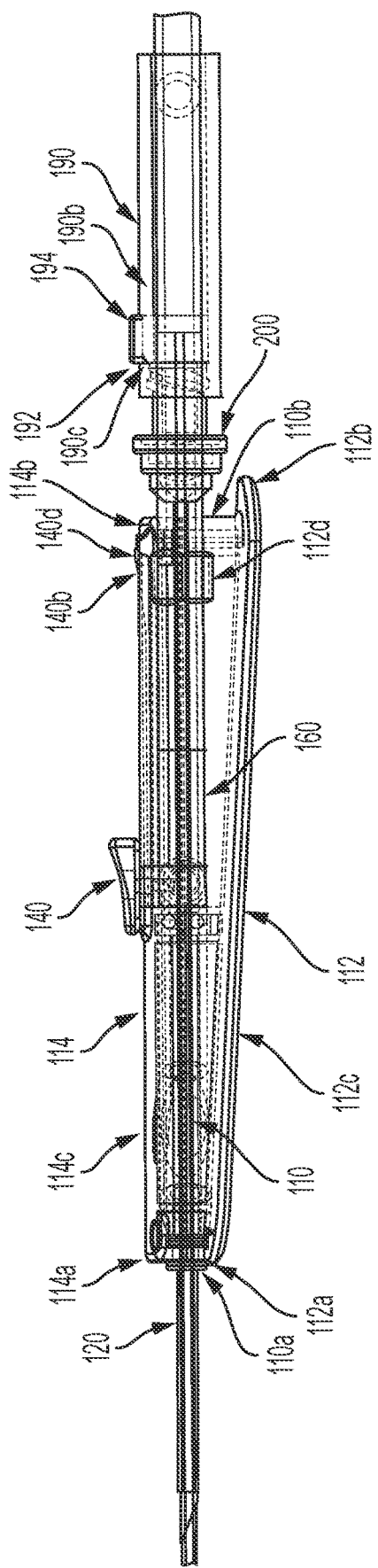
Figure 8B:
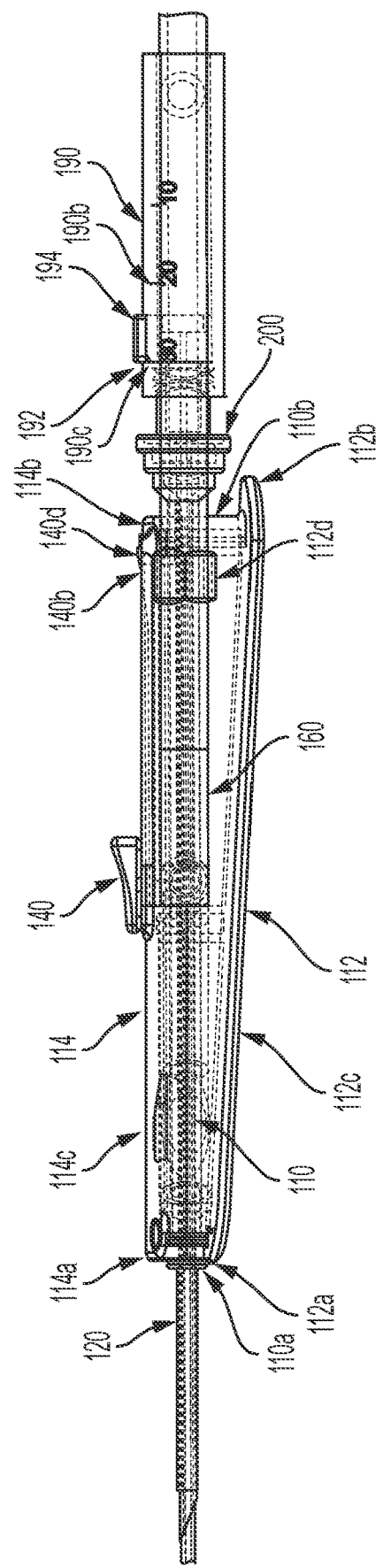
Figure 9:
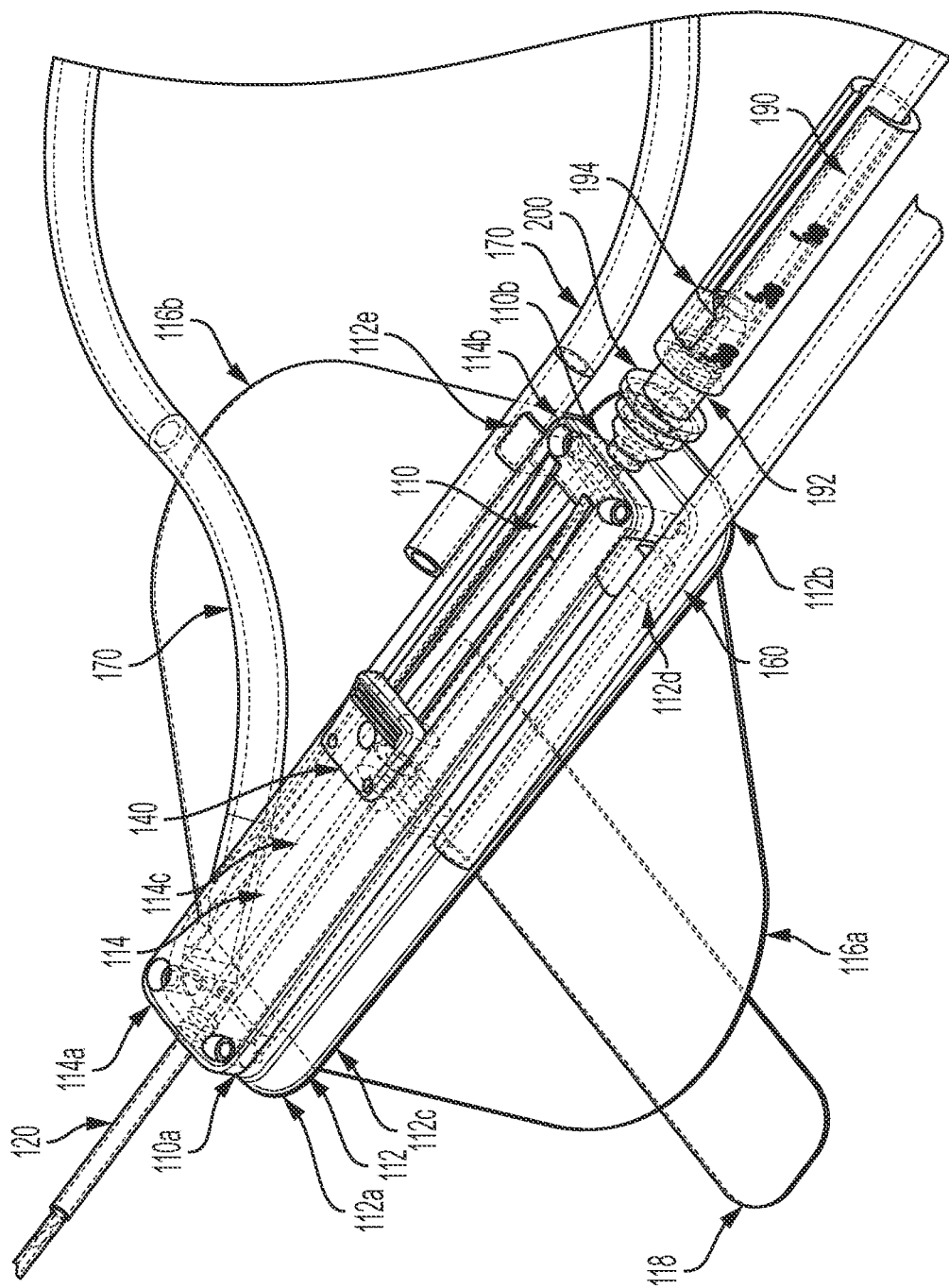
FIG. 9 is a top perspective view that illustrates attachment features of a housing member of an integrated catheter device according to an example of the present general inventive concept. Dashed lines show internal features.

Referring now also to FIGS. 7-9, in the present embodiment, the housing member 110 includes a base member 112 (best visible in FIGS. 5 and 6) and a cover member 114 (visible in FIGS. 1-4) which is assembled onto the base member 112 to slidably (or movably) support the needle member 130 (visible in FIGS. 3-6). The base member 112 has a first end 112a and an opposing second end 112b (best visible in FIGS. 7-9).

Referring again to FIG. 8, preferably, the housing member 110 is configured with an outer surface 112c of the base member 112 non-parallel to an outer surface 114c of the cover member 114 so as to configure the second end 110b of the housing member 110 to be taller than the first end 110a of the housing member 110, such that when the housing member 110 is held adjacent a target area of a patient, longitudinal axes of the outer lumen member 120 and inner lumen member 150 are angled with respect to the target area (e.g., angled toward the target area) to, among other benefits, (1) facilitate insertion of the needle member 130 into an arteriovenous fistula of the patient, as described more fully below, and (2) facilitate easier access to and visibility of the housing member 110 and its features by users.

Referring again to FIG. 9, further preferably, the housing member 110 includes one or more attachment features, such as, for example, one or more extending flaps 116a,116b and/or one or more adhesive strips 118, that are configured to facilitate attachment of the housing member 110, and most preferably the base member 112, to the skin of the target area of the patient. Preferably, the flaps 116a,116b are contoured to approximate a curvature of a patient's arm.

Referring again to FIGS. 1-4 and 7-9, further preferably, the housing member 110 includes one or more tube management features, such as, for example, one or more channels 112d,112e into which a tube of the device 110 (e.g., inflow tube 160 and outflow tube 170 as discussed below) can be snapped or by which can otherwise releasably be held adjacent the housing member 110. Preferably, when the tube is held in the channel 112d,112e, the tube is permitted to slide relative to the tube along a longitudinal axis of the channel 112d,112e.

In the present embodiment, the outer lumen member 120 is manufactured from a flexible material and extends from the first end 112a of the base member 112. Preferably, the flexible material is Pebax or PebaSlix. However, the present general inventive concept is not limited thereto.

In the present embodiment, as best visible in FIGS. 5 and 6, the needle member 130 is coupled to a slide button 140 that is configured to assist a user to move the needle member 130 from a first position P1 to a second position P2. The needle member 130 extends beyond the outer lumen member 120 when the slide button 140 is moved toward the first end 110a of the housing member 110 to place the needle member 130 into the first position P1. Conversely, the needle member 130 is concealed within the outer lumen member 120 when the slide button 140 is moved toward the second end 110b of the housing member 110 to place the needle member 130 into the second position P2. Preferably, the slide button 140 can be locked in each position. For example, as illustrated in FIGS. 7 and 8, a slide surface of the cover member 114 with which the slide button 140 cooperates can be configured with ramps 140a,140b and walls 140c,140d to prevent reverse movement of the slide button 140 when placed in each position.

Preferably, as best visible in FIGS. 5 and 6, the outer lumen member 120 includes a plurality of ports in including a first port 124a disposed at a first end 120a of the outer lumen member 120, a second port 124b disposed at a second end 120b of the outer lumen member 120, and a third port 124c disposed between the first port 124a and the second port 124b.

Further preferably, as best visible in FIGS. 5 and 6, the needle member 130 includes a first tip 132 at a first end 130a of the needle member 130 and a second tip 134 at an opposing second end 130b of the needle member 130. In the present embodiment, the first tip 132 of the needle member 130 is formed as a sharp tip and the second tip 134 is formed as a blunt tip. Preferably, the needle member 130 is hollow to permit blood flow and has a relief port 136 disposed between the first tip 132 and the second tip 134, and the relief port 136 aligns with the third port 124c of the outer lumen member 120 when the needle member 130 is at the first position P1, such that blood flowing into the needle member 130 is diverted.

The needle member 130 preferably is sized inclusively between 17G and 14G and supports blood flow rates inclusively between 200 and over 450 cc per minute. More specifically, for blood flow rates less than 300 cc/min, the recommended needle gauge is 17G; for blood flow rates 300 cc/min to 350 cc/min, the recommended needle gauge is 16G; for blood flow rates over 350 cc/min up to 450 cc/min, the recommended needle gauge is 15G; and for blood flow rates over 450 cc/min, the recommended needle gauge is 14G.

Figure 10A:
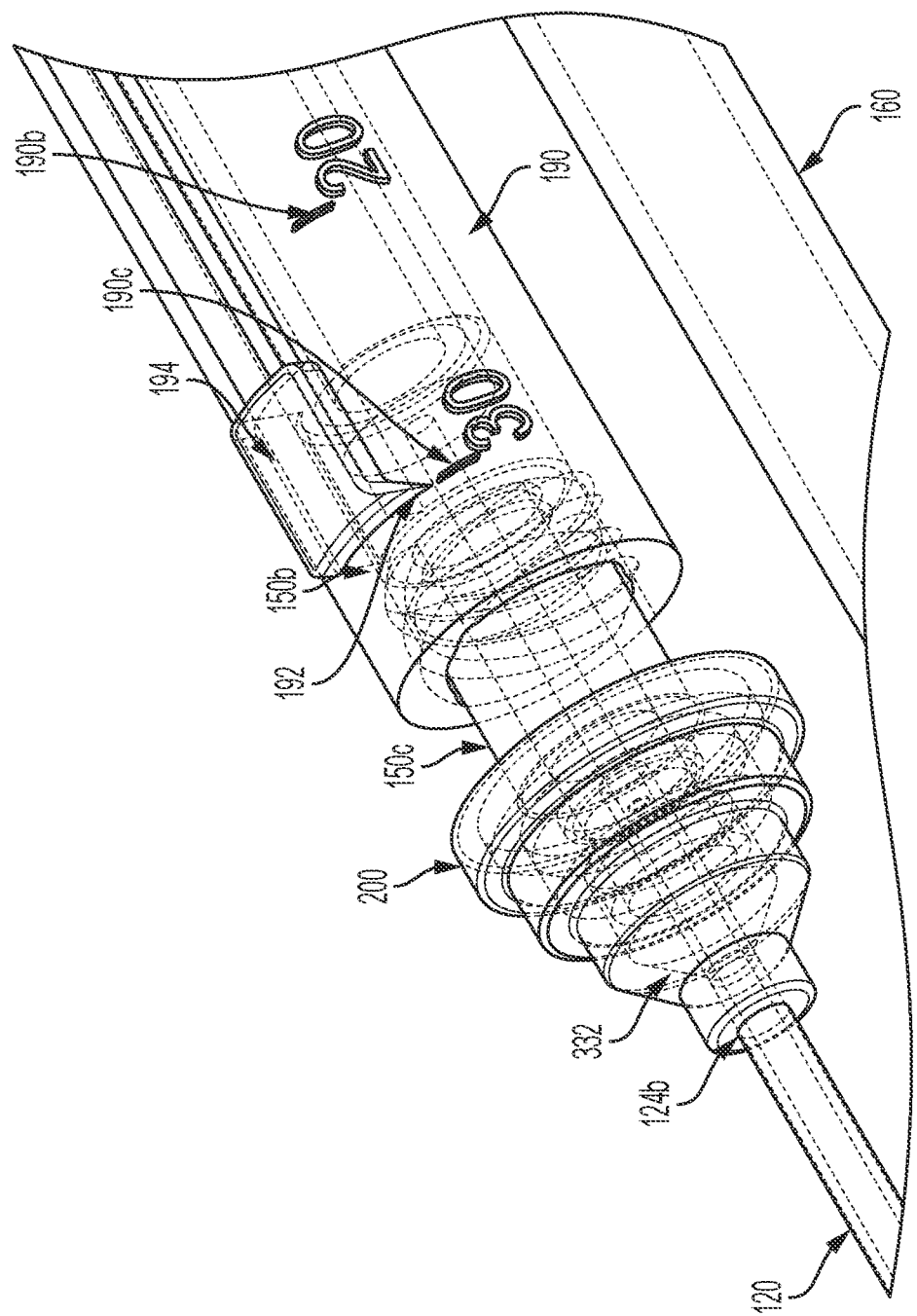
FIGS. 10A and 10B are top perspective views that illustrate an end flash feature of an integrated catheter device according to an example of the present general inventive concept.
Figure 10B:
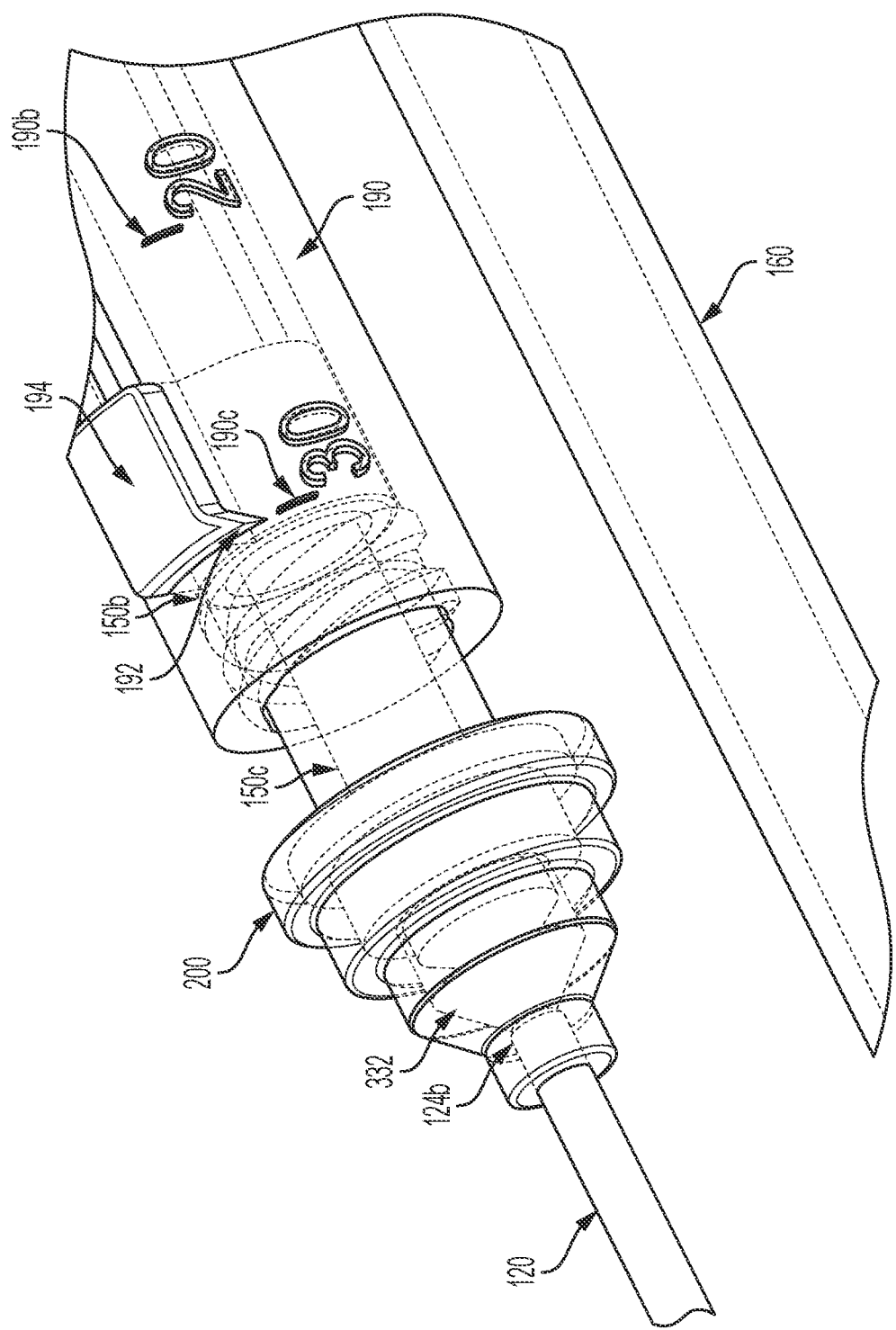

Further preferably, as best shown in FIGS. 5 and 6, the first tip 132 of the needle member 130 can be extended from and retracted into the first port 124a of the outer lumen member 120 by operation of the slide button 140. As will be described further below, when the needle member 130 is extended, and the first tip 132 of the needle member 130 is inserted into an arteriovenous fistula of a patient, a flash of blood 330 from the arteriovenous fistula enters the needle member 130 and is diverted by the relief port 136 to the third port 124c of the outer lumen member 120 due to the alignment of the relief port 136a and the third port 124c. Preferably, the flash of blood 330 is visible adjacent the third port 124c as an indication that the vein has been accessed. In preferred embodiments, alternatively or additionally, as illustrated in FIG. 10, the flash of blood 332 is visible adjacent the second port 124b as an indication that the arteriovenous fistula has been accessed.

Referring again to FIGS. 1-3 and also to FIGS. 7-12, the inner lumen member 150 preferably has a first end 150a that is dimensioned to pass into the second port 124b of the outer lumen member 120, through the outer lumen member 120, and out from the first port 124a of the outer lumen member 120. Preferably, the inner lumen member 150 has a diameter which in such a configuration permits blood from the arteriovenous fistula to flow between an outer wall of the inner lumen member 150 and an inner wall of the outer lumen member 120 and out the third port 124c of the outer lumen member 120.

Figure 16:
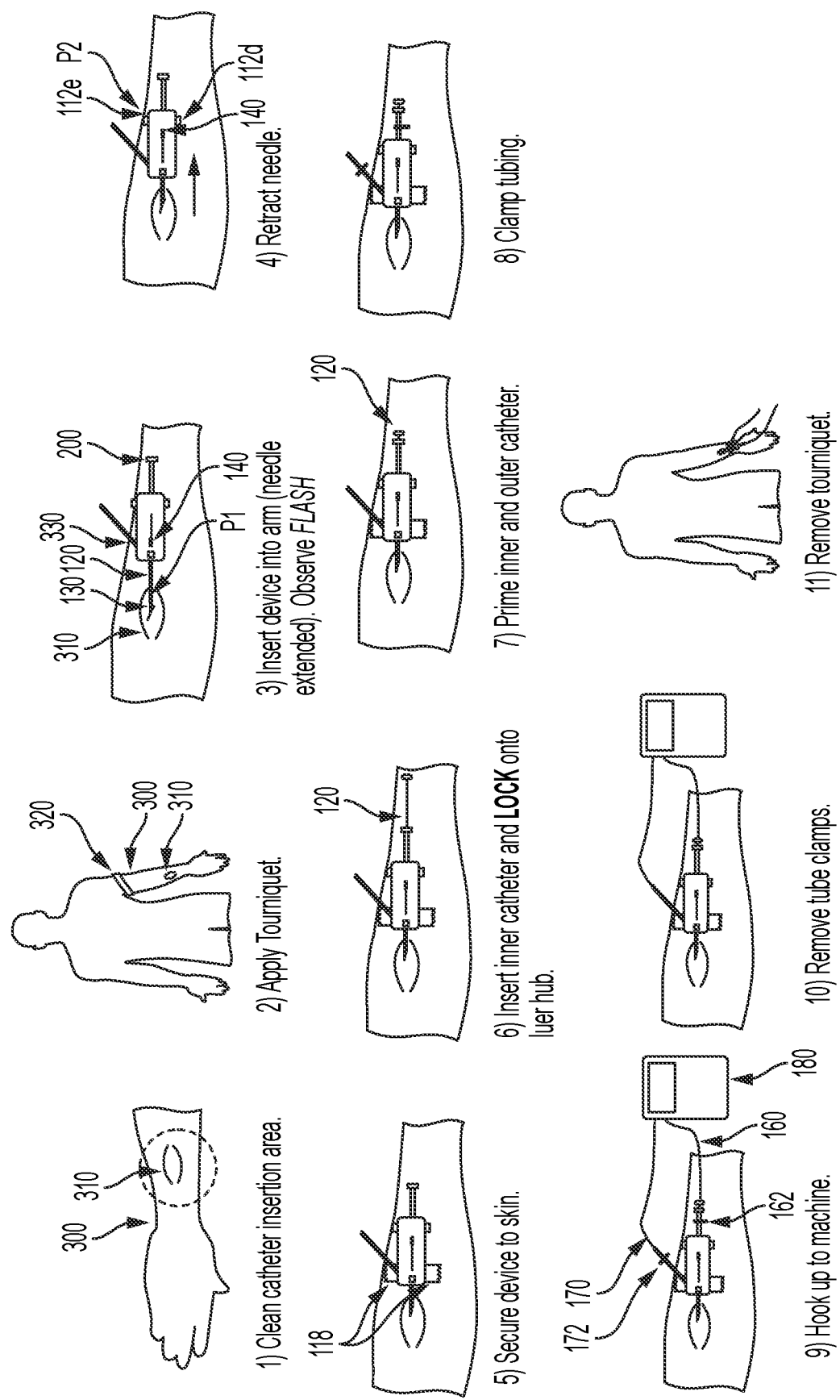
FIG. 16 illustrates use of an integrated catheter device according to an example of the present general inventive concept.

Referring also to FIG. 16, the inner lumen member 150 preferably has a second end 150b that is connected to an inflow tube 160 that can be connected to a dialysis machine 180, as described further below. Accordingly, dialyzed blood from the machine 180 can be introduced into and through the inner lumen member 150.

Figure 11:
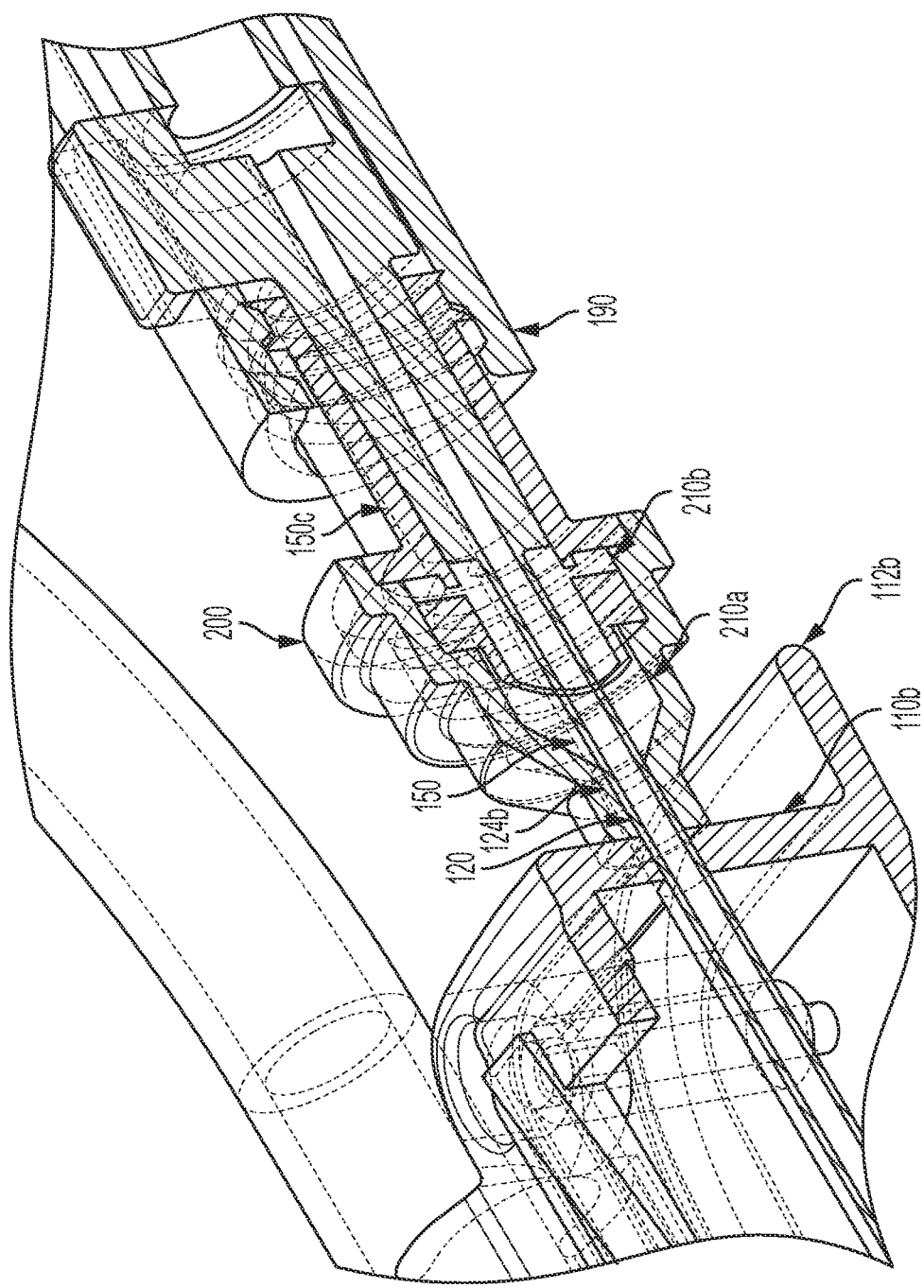
FIG. 11 is a top perspective view that illustrates inner lumen sealing features of an integrated catheter device according to an example of the present general inventive concept. Dashed lines show internal features.
Figure 12:
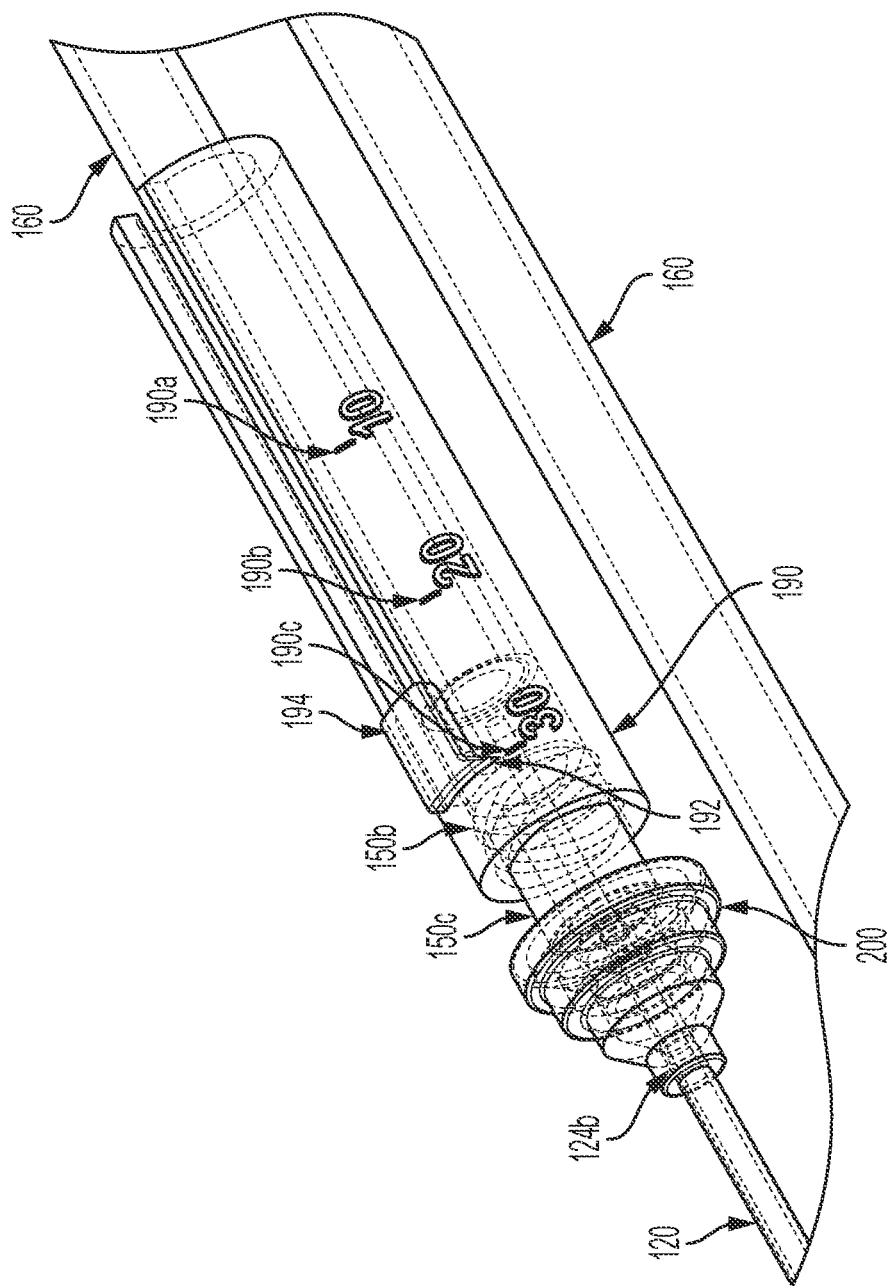
FIG. 12 is a top perspective view that illustrates depth gauge features of an integrated catheter device according to an example of the present general inventive concept. Dashed lines show internal features.
Figure 13:
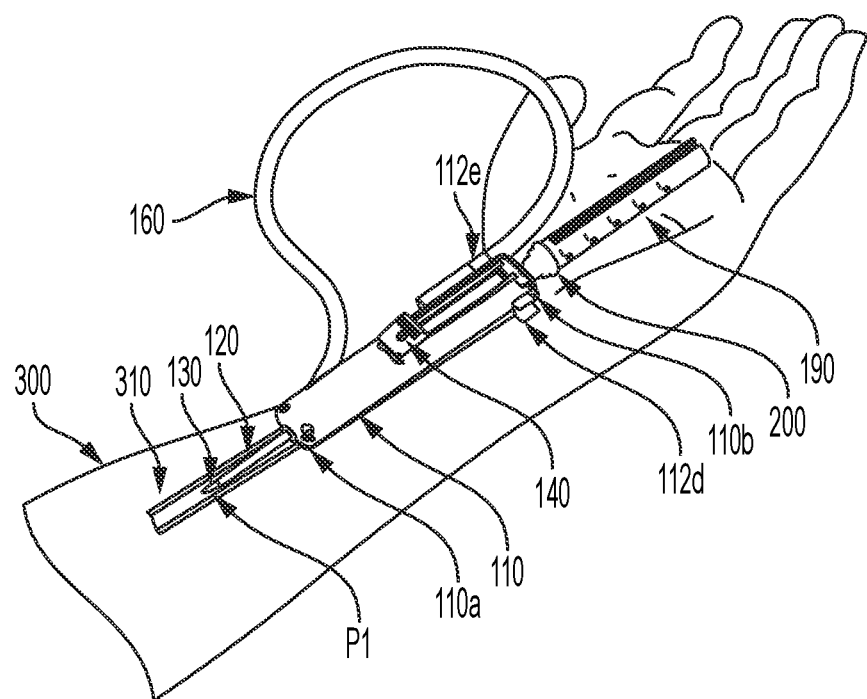
FIG. 13 is a front perspective view of the housing member in the configuration of FIG. 6, with the needle member inserted into a vein of a patient.
Figure 14:
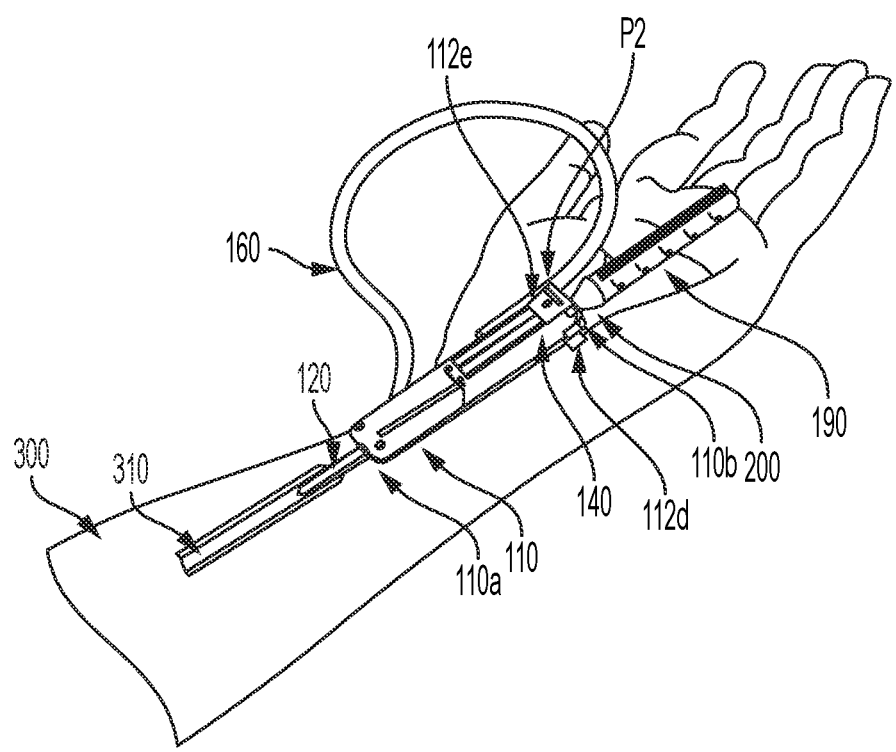
FIG. 14 is a front perspective view of the housing member in the configuration of FIG. 5, with the needle member retracted into the outer lumen.
Figure 15:
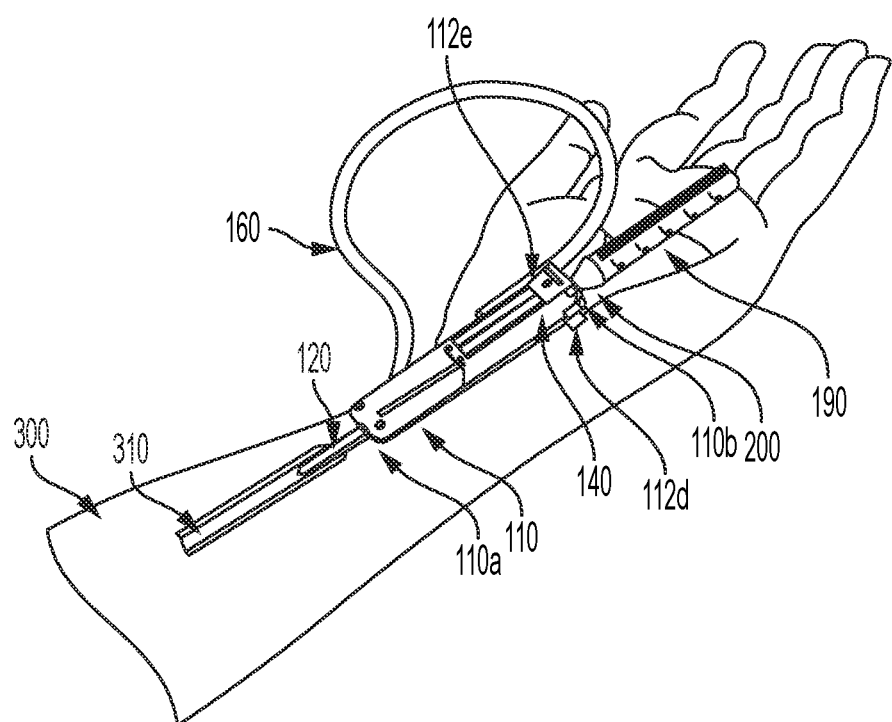
FIG. 15 is a front perspective view of the housing member in the configuration of FIG. 5, with the inner lumen member inserted into an arteriovenous fistula of a patient.

The inner lumen member 150 preferably has a locking portion 150c that can be secured to the coupling body member 200 at the second end 110b of the housing member 110. Preferably, when the locking portion 150c is secured to the coupling body member 200, the inner lumen member 150 is fixed relative to the outer lumen member 120 and the second port 124b of the outer lumen member 120 is sealed to prevent outflow of blood. Preferably, as illustrated in FIG. 11, the coupling body member 200 includes sealing features 210a,210b that cooperate with the locking portion 150c of the inner lumen member 150 to accomplish such outflow prevention.

Preferably, as best shown in FIGS. 7-10 and 12, the integrated catheter device 100 further includes a depth gauge 190 that cooperates with a depth marker 192 on the inner lumen member 150 in a configuration in which the depth marker 192 indicates a distance from which a first end 150a of the inner lumen member 150 extends past the first port 124a of the outer lumen member 120 when the inner lumen member 150 is pass into the second port 124b of the outer lumen member 120, through the outer lumen member 120, and out from the first port 124a of the outer lumen member 120. For example, the depth gauge 190 preferably includes markings 190a, 190b, 190c at 10 mm, 20 mm and 30 mm distances, respectively, along its length, and the depth marker 192 aligns with one of the markings when positioned at a corresponding depth distance.

Further preferably, as best shown in FIGS. 7-10 and 12, the integrated catheter device 100 includes a depth slider 194 configured to facilitate moving the first end 150a of the inner lumen member 150 forward outwardly from and backward inwardly toward the first end 124a of the outer lumen member 120. Preferably, the depth slider 194 is configured to be operable by a thumb of a user. Further preferably, the depth slider 194 is integrated with the depth marker 192 discussed above.

With regard to use of the integrated catheter device 100, and with reference also to FIGS. 13-16, a target area 310 of an arm 300 of a patient is prepared. For example, skin of the target area 310 of the arm 300 is sterilized (see, e.g., FIG. 16, Step 1), and a tourniquet 320 is applied to the arm between a shoulder of the patient and the target area 310 (see, e.g., FIG. 16, Step 2). Alternative preparations of the target area 310 in anticipation of use of the integrated catheter device 100 are also contemplated, and preferred preparations are those determined by a qualified physician.

Once the target area 310 is prepared, the needle member 130 is extended by being placed in the first position P1 by moving the slide button 140 toward the first position P1. When the needle member 130 is in the first position P1, the first tip 132 of the first end 130a of the needle member 130 is extended from the outer lumen member 120.

With the first tip 132 of the first end 130a of the needle member 130 extended from the outer lumen member 120, the first tip 132 is pressed against the target area 310 to break the skin, and continued pressing causes the first tip 132 and the outer lumen member 120 to enter an arteriovenous fistula of the patient and remain there. When the first tip 132 enters the arteriovenous fistula, a flash of blood 330 flows into the needle member 130, out the relief port 136 of the needle member 130 and toward the third port 124c of the outer lumen member 120, where it is observed. (See, e.g., FIG. 13 and FIG. 16, Step 3.)

Once the flash of blood is observed, the needle member 130 is retracted by being placed in the second position P2 by moving the slide button 140 toward the second position P2 (see, e.g., FIG. 16, Step 4).

Once the needle member 130 is retracted, the housing member 110 is secured to the target area 310 using one or more of the attachment features 116a, 116b, 118 of the housing member 110 (see, e.g., FIG. 16, Step 5).

Once the housing member 110 is secured to the target area 310, the inner lumen member 150 is inserted into and through the second port 124b of the outer lumen member 120 until the first end 150a of the inner lumen member 150 extends from the outer lumen member 120 into the arteriovenous fistula. The locking portion 150c of the inner lumen member 150 is then locked to the coupling body member 200 (e.g., the luer lock) of the housing member 110. (See, e.g., FIG. 16, Step 6.)

Once the inner lumen member 150 is locked to the coupling body member 200, the inner lumen member 150 and outer lumen member 120 are primed to effect blood flow (see, e.g., FIG. 16, Step 7), a tube 160 attached to the inner lumen member 150 is clamped (e.g., with an inner lumen tube clamp 162) to temporarily prevent blood flood from the arteriovenous fistula, and an outflow tube 170 of the outer lumen member 120 is clamped (e.g., with an outer lumen tube clamp 172) to temporarily prevent blood flood into the arteriovenous fistula (see, e.g., FIG. 16, Step 8).

Once the tubes 160,170 are clamped, the tubes 160,170 are connected to a dialysis machine 180, with the tube 160 connected to the inner lumen 150 configured to pass blood to the machine 180, and the tube 170 connected to the outer lumen 120 configured to pass blood from the machine 180 (see, e.g., FIG. 16, Step 9). The tubes 160,170 are then unclamped to permit blood flow accordingly (see, e.g., FIG. 16, Step 10), and the tourniquet 320 is removed (see, e.g., FIG. 16, Step 11). The blood replacement process then continues for a desired or recommended amount of time.

Once the blood replacement process has continued for the desired or recommended amount of time, the machine 180 is deactivated, the tubes 160,180 are clamped and then disconnected from the machine. Then, the locking portion 150c of the inner lumen member 150 is unlocked from the coupling body member 200 of the housing member 110, and the inner lumen member 150 is removed from the outer lumen member 120. Then, the housing member 110 is removed from the target area 310 of the patient, and the outer lumen member 120 is removed from the arteriovenous fistula of the patient. Finally, the wound is sterilized and bandaged.

It is to be understood that the foregoing illustrative exemplary embodiments have been provided merely for the purpose of explanation and are in no way to be construed as limiting of the present general inventive concept. Words used herein are words of description and illustration, rather than words of limitation. In addition, the advantages and objectives described herein may not be realized by each and every exemplary embodiment practicing the present general inventive concept. Further, although the present general inventive concept has been described herein with reference to particular structure, steps and/or exemplary embodiments, the present general inventive concept is not intended to be limited to the particulars disclosed herein. Rather, the present general inventive concept extends to all functionally equivalent structures, methods and uses, such as are within the scope of the appended claims. Those skilled in the art, having the benefit of the teachings of this specification, may affect numerous modifications thereto and changes may be made without departing from the scope and spirit of the present general inventive concept.

What is claimed is:

1. A catheter assembly comprising:
   a housing member having a first end and an opposing second end;
   an outer lumen member having inner and outer walls, said outer lumen member extendable through the first end of the housing member;
   a needle movably coupled to the housing wherein the needle is adapted to extend beyond the inner wall of the outer lumen member and is retractable within the outer lumen member; and
   an inner lumen member having inner and outer walls, said inner lumen member in connectable fluid communication with the second end of the housing member,
   wherein the inner lumen member has an outer diameter smaller than the inner diameter of the outer lumen member and the inner lumen member is disposed coaxial with the outer lumen member so that blood flow is permitted between the outer wall of the inner lumen member and the inner wall of the outer lumen member and wherein the needle extends beyond the outer lumen member in a first position and is concealed in a second position.

2. The catheter assembly of claim 1, further comprising a locking feature to releasably lock the needle member at the first and second positions.

3. The catheter assembly of claim 1, wherein the outer lumen member includes a plurality of ports in fluidic communication with each other, the plurality of ports including a first port disposed at a first end of the outer lumen member, a second port disposed at an opposing second end, and a third port disposed between the first port and the second port.

4. The catheter assembly of claim 3, wherein the needle includes a sharp tip at a first end and a blunt tip at an opposing second end.

5. The catheter assembly of claim 4 wherein the needle includes a relief port disposed between a first end and a second end.

6. The catheter assembly of claim 5, wherein fluid received by the needle is diverted by the relief port to the third port when the needle is disposed at the first position.

7. The catheter assembly of claim 3, further comprising a coupling body member attached to the second port of the outer lumen member and configured to receive an inner lumen member.

8. The catheter assembly of claim 7, further comprising an inner lumen depth gauge coupled to the coupling body member.

9. The catheter assembly of claim 8, wherein the depth gauge includes depth markings and the inner lumen member includes an inner lumen depth marker cooperating with the depth markings to indicate a distance from which a first end of the inner lumen member extends past the first port of the outer lumen member.

10. The catheter assembly of claim 7, wherein when the inner lumen member is disposed coaxial with the outer lumen member and the needle is in the second position, blood flow is permitted between an outer wall of the inner lumen member and an inner wall of the outer lumen member.

11. The catheter assembly of claim 10, wherein the inner lumen member has an outer diameter smaller than an inner diameter of the needle and the needle has an outer diameter smaller than an inner diameter of the outer lumen member.

12. The catheter assembly of claim 7, further comprising an outflow tube coupled in fluidic communication with the third port and an inflow tube coupled in fluidic communication with the inner lumen member.

13. The catheter assembly of claim 12, wherein the housing member includes at least one channel by which at least one of the tubes can be held adjacent the housing member.

14. The catheter assembly of claim 7, wherein outer surfaces of the housing member are non-parallel such that when the housing member is adjacent a target area of a patient, a longitudinal axis of the outer lumen member and a longitudinal axis of the inner lumen member are angled toward the target area.

15. The catheter assembly of claim 14, wherein the housing member includes at least one adhesive flap contoured to approximate a curvature of an arm.

* * * * *